US00PP24748P2

(12) United States Plant Patent
van den Dool

(10) Patent No.: US PP24,748 P2
(45) Date of Patent: Aug. 12, 2014

(54) ***NANDINA* PLANT NAMED 'SUNSET'**

(50) Latin Name: *Nandina domestica*
Varietal Denomination: Sunset

(76) Inventor: Wouter Leopold van den Dool, Waddinxveen (NL)

( * ) Notice: Subject to any disclaimer, the term of this patent is extended or adjusted under 35 U.S.C. 154(b) by 152 days.

(21) Appl. No.: 13/507,790

(22) Filed: Jul. 27, 2012

(51) Int. Cl.
*A01H 5/00* (2006.01)

(52) U.S. Cl.
USPC ..... Plt./235

(58) Field of Classification Search
USPC ..... Plt./235
See application file for complete search history.

*Primary Examiner* — Wendy C Haas
(74) *Attorney, Agent, or Firm* — C. A. Whealy

(57) ABSTRACT

A new and distinct cultivar of *Nandina* plant named 'Sunset', characterized by its upright and outwardly spreading plant habit; moderately vigorous growth habit; relatively small leaflets; dark purple-colored developing leaflets; dark green-colored fully developed leaflets; and good garden performance.

3 Drawing Sheets

Botanical designation: *Nandina domestica*.
Cultivar denomination: 'SUNSET'.

BACKGROUND OF THE INVENTION

The present invention relates to a new and distinct cultivar of *Nandina* plant, botanically known as *Nandina domestica* and hereinafter referred to by the name 'Sunset'.

The new *Nandina* plant is a naturally-occurring whole plant mutation of an unnamed selection of *Nandina domestica*, not patented. The new *Nandina* plant was discovered and selected by the Inventor from within a population of plants of the parent selection during the spring of 2009 in a controlled greenhouse environment in Boskoop, The Netherlands.

Asexual reproduction of the new *Nandina* plant by cuttings in a controlled greenhouse environment in Boskoop, The Netherlands since the spring of 2009 has shown that the unique features of this new *Nandina* plant are stable and reproduced true to type in successive generations of asexual reproduction.

SUMMARY OF THE INVENTION

Plants of the new *Nandina* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunset'. These characteristics in combination distinguish 'Sunset' as a new and distinct *Nandina* plant:

1. Upright and outwardly spreading plant habit.
2. Moderately vigorous growth habit.
3. Relatively small leaflets.
4. Dark purple-colored developing leaflets.
5. Dark green-colored fully developed leaflets.
6. Good garden performance.

Plants of the new *Nandina* can be compared to plants of the parent selection. Plants of the new *Nandina* differ from plants of the parent selection in the following characteristics:

1. Developing leaflets of plants of the new *Nandina* are dark purple in color whereas developing leaflets of the parent selection are dark green in color.
2. Fully developed leaflets of plants of the new *Nandina* are smaller than fully developed leaflets of plants of the parent selection.

Plants of the new *Nandina* can be compared to plants of the *Nandina domestica* 'Tuscan Flame', disclosed in U.S. Plant Pat. No. 21,940. In side-by-side comparisons conducted in Boskoop, The Netherlands, plants of the new *Nandina* differed from plants of 'Tuscan Flame' in the following characteristics:

1. Plants of the new *Nandina* were more compact than plants of 'Tuscan Flame'.
2. Developing leaflets of plants of the new *Nandina* were dark purple in color whereas developing leaflets of 'Tuscan Flame' were dark green in color.
3. Fully developed leaflets of plants of the new *Nandina* were smaller and darker green in color than fully developed leaflets of plants of 'Tuscan Flame'.

Plants of the new *Nandina* can be compared to plants of the *Nandina domestica* 'Obsession', not patented. In side-by-side comparisons conducted in Boskoop, The Netherlands, plants of the new *Nandina* differed from plants of 'Obsession' in the following characteristics:

1. Fully developed leaflets of plants of the new *Nandina* were smaller than fully developed leaflets of plants of 'Obsession'.
2. Fully developed leaflets of plants of the new *Nandina* were darker green in color than fully developed leaflets of plants of 'Obsession'.

Plants of the new *Nandina* can also be compared to plants of the *Nandina domestica* 'Flirt', not patented. In side-by-side comparisons conducted in Boskoop, The Netherlands, plants of the new *Nandina* differed from plants of 'Flirt' in the following characteristics:

1. Plants of the new *Nandina* were more upright than and not as bushy as plants of 'Flirt'.

2. Fully developed leaflets of plants of the new *Nandina* were smaller than fully developed leaflets of plants of 'Flirt'.

BRIEF DESCRIPTION OF THE PHOTOGRAPHS

The accompanying colored photographs illustrate the overall appearance of the new *Nandina* plant showing the colors as true as it is reasonably possible to obtain in colored reproductions of this type. Colors in the photographs may differ slightly from the color values cited in the detailed botanical description which accurately describe the colors of the new *Nandina* plant.

The photograph on the first sheet is a side perspective view of a typical plant of 'Sunset' grown in a container.

The photograph on the second sheet is a close-up view of developing stems and leaves of a typical plant of 'Sunset'.

The photograph on the third sheet is a close-up view of fully developed stems and leaves of a typical plant of 'Sunset'.

DETAILED BOTANICAL DESCRIPTION

The aforementioned photographs and following observations, measurements and values describe plants grown in three-liter containers during the winter in a polyethylene-covered greenhouse in Waddinxveen, The Netherlands and under cultural practices which closely approximate commercial *Nandina* production. During the production of the plants, day temperatures ranged from 6° C. to 18° C. and night temperatures ranged from 1° C. to 10° C. Plants were two years old when the description was taken and three years old when the photographs were taken. In the following detailed description, color references are made to The Royal Horticultural Society Colour Chart, 2007 Edition, except where general terms of ordinary dictionary significance are used.

Botanical classification: *Nandina domestica* 'Sunset'.

Parentage: Naturally-occurring whole plant mutation of an unnamed selection of *Nandina domestica*, not patented.

Propagation:

*Type*.—By cuttings.

*Time to initiate roots*.—About 75 days at 20° C.

*Time to produce a rooted young plant*.—About 110 days at 20° C.

*Root description*.—Fine and somewhat fibrous; close to 161B in color.

*Rooting habit*.—Freely branching; dense.

Plant description:

*Plant form and growth habit*.—Perennial evergreen shrub; upright and outwardly spreading plant habit; moderately vigorous growth habit.

*Plant height*.—About 60.3 cm.

*Plant diameter* (*area of spread*).—About 50.1 cm.

Lateral branch description:

*Length*.—About 39.5 cm.

*Diameter*.—About 5 mm.

*Internode length*.—About 3.8 cm.

*Aspect*.—Erect.

*Strength*.—Strong.

*Texture*.—Smooth, glabrous; fully developed stems, woody.

*Color, developing*.—Close to 146A tinged with close to 177A.

*Color, fully developed*.—Close to 200D.

Foliage description:

*Arrangement*.—Alternate; compound, tripinnate.

*Leaves*.—Length: About 30.6 cm. Width: About 30 cm. Shape: Roughly deltoid.

*Leaflets*.—Length: About 3.2 cm. Width: About 9 mm. Shape: Lanceolate. Apex: Acuminate. Base: Narrowly acute. Margin: Entire. Texture, upper and lower surfaces: Smooth, glabrous. Venation pattern: Pinnate. Color: Developing leaves, upper surface: Close to N186C. Developing leaves, lower surface: Close to 183C to 183D. Fully developed leaves, upper surface: Between N137A and 139A; venation, between N137A and 139A. Fully developed leaves, lower surface: Close to 138A to 138B; venation, close to 146A to 146B.

*Petioles, leaves*.—Length: About 27.3 cm. Diameter: About 2 mm.

*Petioles, leaflets*.—Length: About 9 mm. Diameter: About 0.75 mm. Texture, upper and lower surfaces: Smooth, glabrous. Color, upper surface: Close to N137A. Color, lower surface: Close to 138A.

Flower description: Flower initiation and development has not been observed on plants of the new *Nandina*.

Garden performance: Plants of the new *Nandina* have been observed to have good garden performance and to tolerate rain, wind, high temperatures about 35° C. to 40° C. and to be hardy to USDA Hardiness Zone 7.

Pathogen & pest resistance: Plants of the new *Nandina* have not been observed to be resistant to pathogens and pests common to *Nandina* plants.

It is claimed:

1. A new and distinct *Nandina* plant named 'Sunset' as illustrated and described.

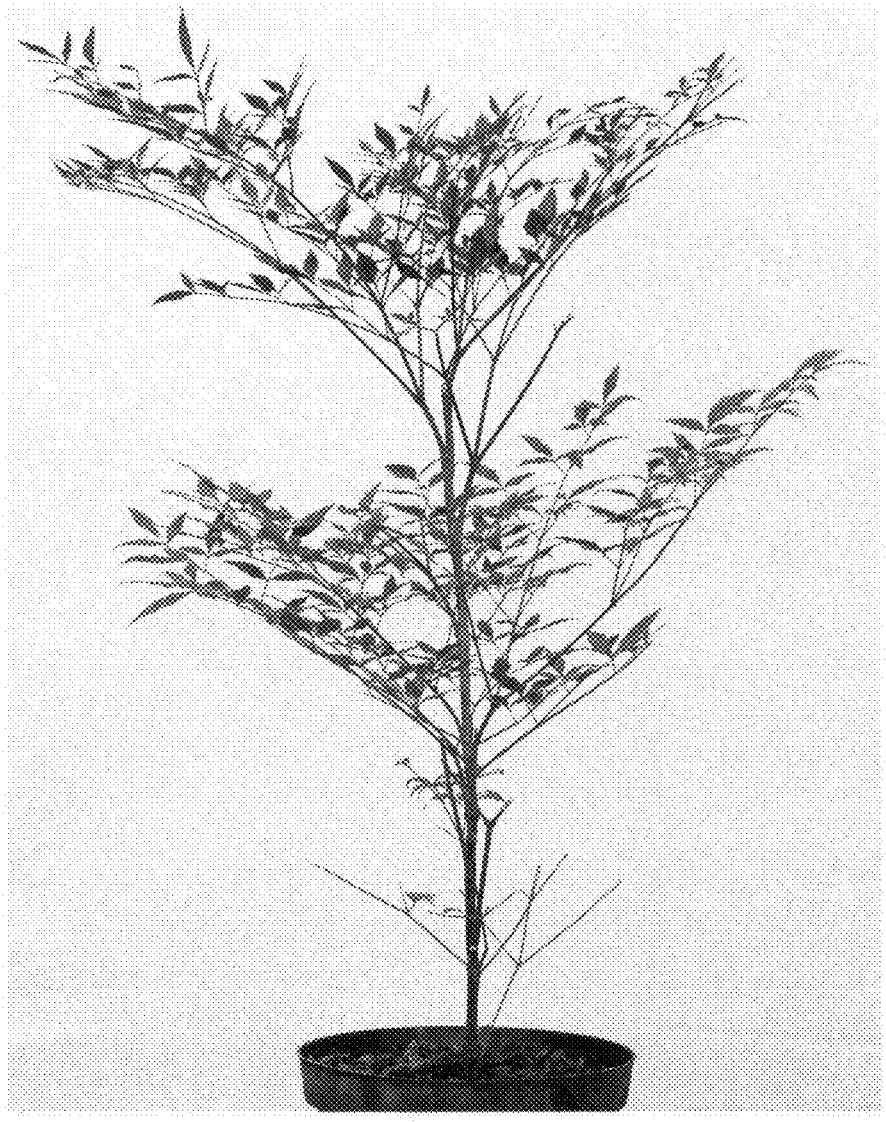

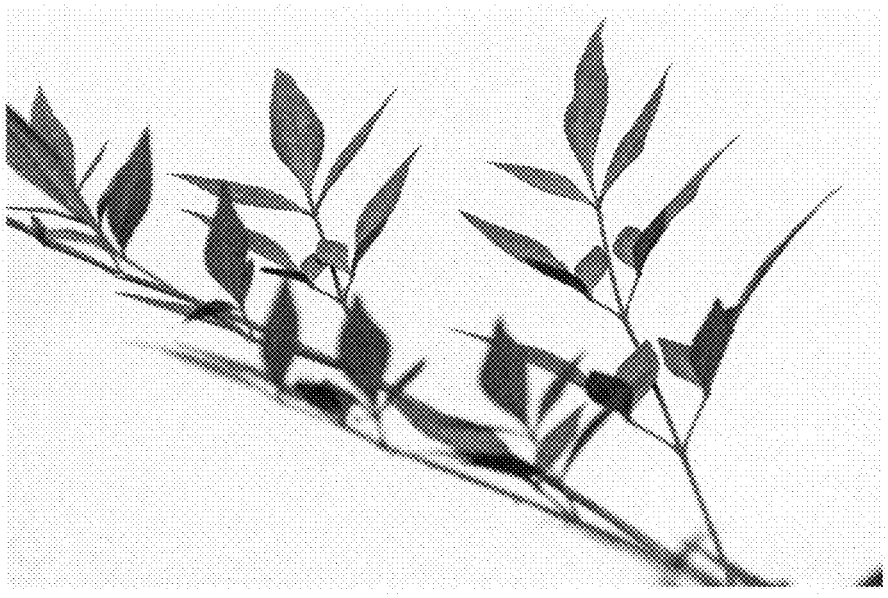

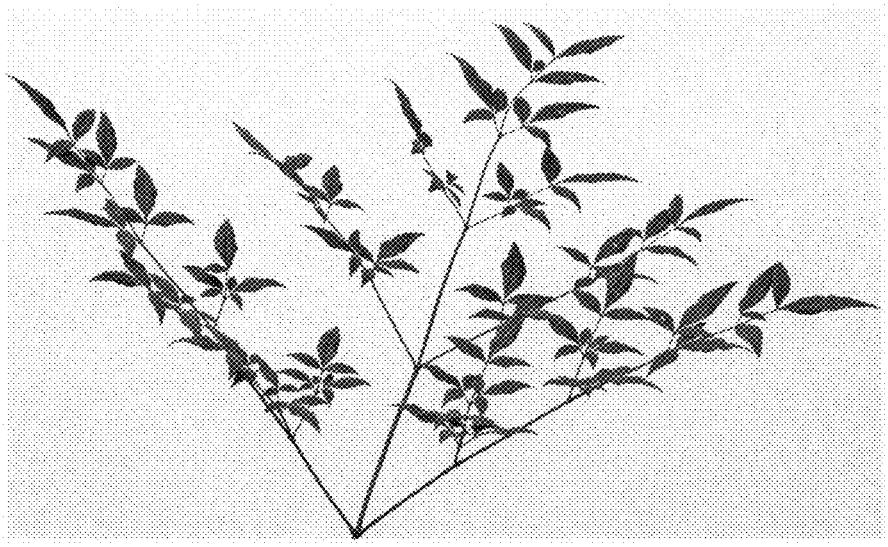

* * * * *